United States Patent
Zou et al.

(10) Patent No.: US 8,320,521 B2
(45) Date of Patent: Nov. 27, 2012

(54) METHOD AND SYSTEM FOR OPERATING AN ELECTRON BEAM SYSTEM

(75) Inventors: Yun Zou, Clifton Park, NY (US); Carey Shawn Rogers, Brookfield, WI (US); Christopher David Unger, Brookfield, WI (US); Mark Alan Frontera, Ballston Lake, NY (US); Sergio Lemaitre, Whitefish Bay, WI (US)

(73) Assignee: General Electric Company, Niskayuna, NY (US)

(*) Notice: Subject to any disclaimer, the term of this patent is extended or adjusted under 35 U.S.C. 154(b) by 237 days.

(21) Appl. No.: 12/894,781

(22) Filed: Sep. 30, 2010

(65) Prior Publication Data

US 2012/0082292 A1  Apr. 5, 2012

(51) Int. Cl.
*A61B 6/03* (2006.01)
*H05G 1/26* (2006.01)

(52) U.S. Cl. .......................... 378/16; 378/106
(58) Field of Classification Search ............... 378/4, 19, 378/16, 101, 106, 137, 138
See application file for complete search history.

(56) References Cited

U.S. PATENT DOCUMENTS

| | | | |
|---|---|---|---|
| 4,646,338 A | 2/1987 | Skillicorn | |
| 4,748,650 A * | 5/1988 | Ammann | 378/137 |
| 7,692,329 B2 | 4/2010 | Abu Qahouq et al. | |
| 7,759,655 B2 | 7/2010 | McCauley | |
| 2006/0233699 A1 | 10/2006 | Mills | |
| 2009/0026912 A1 | 1/2009 | Lordi et al. | |
| 2011/0058643 A1 * | 3/2011 | Lamaitre et al. | 378/4 |
| 2011/0280363 A1 * | 11/2011 | Zou et al. | 378/4 |

* cited by examiner

*Primary Examiner* — Irakli Kiknadze
(74) *Attorney, Agent, or Firm* — Jason K. Klindtworth

(57) ABSTRACT

A method for operating an electron beam system is presented. Further, an electron beam system, an X-ray tube and a CT system that implement the presented method are also described. The method includes generating an electron beam in an X-ray tube in an imaging system. Additionally, a current configuration corresponding to a particular view of the imaging system is identified. If the identified current configuration is within a determined range, a duty cycle of the electron beam for the particular view of the imaging system is modulated using pulse width modulation. Further, the modulated electron beam is focused towards a target.

27 Claims, 6 Drawing Sheets

METHOD AND SYSTEM FOR OPERATING AN ELECTRON BEAM SYSTEM

BACKGROUND

Embodiments of the present invention relate generally to diagnostic imaging, and more particularly to a method and a system for operating an electron beam system in a wide dynamic range of emission.

Computed tomography (CT) finds wide application in fields such as clinical diagnosis, industrial inspection and security screening. Several CT systems have been developed, for example, for detecting breast cancer, diagnosing cardiovascular diseases, performing CT fluoroscopy and airport luggage inspection. CT systems require a large number of projection images from a wide range of viewing angles for high quality image reconstruction. Additionally, the CT systems may also need to control the electron beam intensity of the X-rays for reducing patient dose while still achieving desired imaging quality.

To that end, conventional CT systems employ devices such as X-ray tubes having controlled filament heating for electron beam emission control. Conventional filament heating, however, is a slow process of the order of tens of milliseconds, thus preventing its usage in applications where faster electron beam emission control, such as of the order of tens of microseconds, is desirable. The X-ray tubes may further include control means such as an electrostatic grid and/or a magnetic assembly to control the electron beam current. Rapid changes in the electron beam current in such an X-ray tube, however, prevent proper positioning and focusing of the electron beam on a target object. Particularly, modulation of the electron beam current from 0 percent to 100 percent of the electron beam intensity causes repulsion of electrons among one another due to changes in space charge force. The changes in the space charge force further affect the electro-magnetic focusing and deflection of the electron beam in the X-ray tube, thus affecting the focal spot size.

Particularly, while operating the X-ray tube with a low electron beam current, such as about 10 milliampere (mA) and 140 kilovolts (kV) the strong influence of the electro-magnetic forces overly focus the electron beam to form a constricted "waist" in the electron beam trajectory. Reversing this narrowing effect in the electron beam during imaging is a challenging task. The narrowing effect hinders the ability of the X-ray tube to precisely control the positioning and the focusing of the electron beam at a target location at low electron beam currents, thus impeding imaging system performance.

It is desirable to develop effective methods and systems that enable an electron beam system of an X-ray tube to operate in a wide dynamic range of emission. Particularly, there is a need for an electron beam system that controls the electron beam intensity to accurately position the electron beam at a target location based on imaging requirements. Further, it is also be desirable to develop methods and systems that control focus and position of the electron beam to achieve robust imaging system performance while preserving image quality and durability of the X-ray source.

BRIEF DESCRIPTION

In accordance with aspects of the present technique, a method for operating an electron beam system is presented. The method includes generating an electron beam in an X-ray tube in an imaging system. Additionally, a current configuration corresponding to a particular view of the imaging system is identified. If the identified current configuration is within a determined range, a duty cycle of the electron beam for the particular view of the imaging system is modulated using pulse width modulation. Further, the modulated electron beam is focused towards a target.

In accordance with aspects of the present system, an electron beam system is described. The electron beam system includes an emitter that generates an electron beam and at least one electrode maintained at a positive bias voltage or a negative bias voltage with respect to the emitter, where the electrode controls an intensity of the electron beam. Further, the electron beam system includes a control unit coupled to the at least one electrode. Particularly, the control unit identifies a current configuration corresponding to the particular view of the X-ray tube. The control unit then modulates a duty cycle of the electron beam for the particular view of the X-ray tube using pulse width modulation when the identified current configuration is within a determined range.

In accordance with another aspect of the present system, an X-ray tube is presented. The X-ray tube includes an electron beam system. The electron beam system further includes an emitter that generates an electron beam and at least one electrode maintained at a positive bias voltage or a negative bias voltage with respect to the emitter, where the electrode controls an intensity of the electron beam. Further, the X-ray tube includes a control unit coupled to the at least one electrode. Particularly, the control unit identifies a current configuration corresponding to the particular view of the X-ray tube. The control unit then modulates a duty cycle of the electron beam for the particular view of the X-ray tube using pulse width modulation when the identified current configuration is within a determined range. The X-ray tube also includes a target that generates X-rays when impinged upon by the electron beam.

In accordance with yet another aspect of the present system, a computed tomography system is described. The computed tomography system includes a gantry and an X-ray tube that includes an electron beam system. The electron beam system further includes an emitter that generates an electron beam and at least one electrode maintained at a positive bias voltage or a negative bias voltage with respect to the emitter, where the electrode controls an intensity of the electron beam. Further, the X-ray tube includes a control unit coupled to the at least one electrode and the extraction electrode. Particularly, the control unit identifies a current configuration corresponding to the particular view of the X-ray tube. The control unit then modulates a duty cycle of the electron beam for the particular view of the X-ray tube using pulse width modulation when the identified current configuration is within a determined range. The X-ray tube also includes a target that generates X-rays when impinged upon by the electron beam. The computed tomography system further includes one or more detector elements for detecting the attenuated electron beam from an object.

DRAWINGS

These and other features, aspects, and advantages of the present technique will become better understood when the following detailed description is read with reference to the accompanying drawings in which like characters represent like parts throughout the drawings, wherein.

DETAILED DESCRIPTION

The following description presents systems and methods for operating an electron beam system such as an electron injector. Particularly, certain embodiments illustrated herein describe systems and methods for effectively operating the electron injector in a wide dynamic range of emission with acceptable focal spot quality. Although the following description includes only a few embodiments, the electron beam system may be implemented in various other imaging systems and applications to achieve high image quality and optimized dose control. By way of example, the electron beam system may be used in a CT system, an X-Ray system and electron gun assembly using a Wehlnet cylinder or field electron emitters. An exemplary environment that is suitable for practicing various implementations of the present system is described in the following sections with reference to FIGS. 1-2.

Figure 1:
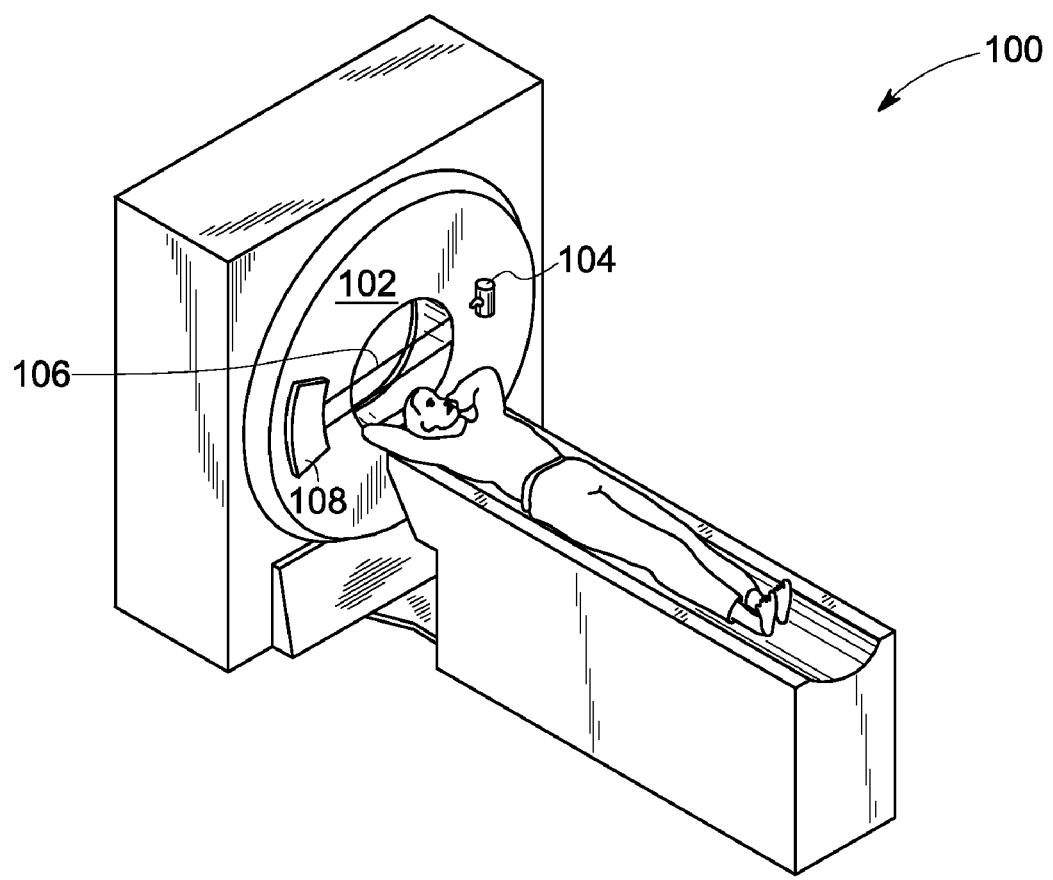
FIG. 1 is a pictorial view of a CT system.

FIG. 1 illustrates an exemplary CT system 100 for acquiring and processing image data. In one embodiment, the CT system 100 includes a gantry 102. The gantry 102 further includes at least one X-ray radiation source 104 that projects a beam of X-ray radiation 106 towards a detector array 108 positioned on the opposite side of the gantry 102. Although FIG. 1 depicts a single X-ray radiation source 104, in certain embodiments, multiple radiation sources may be employed to project a plurality of X-ray beams for acquiring image data from different view angles.

Figure 2:
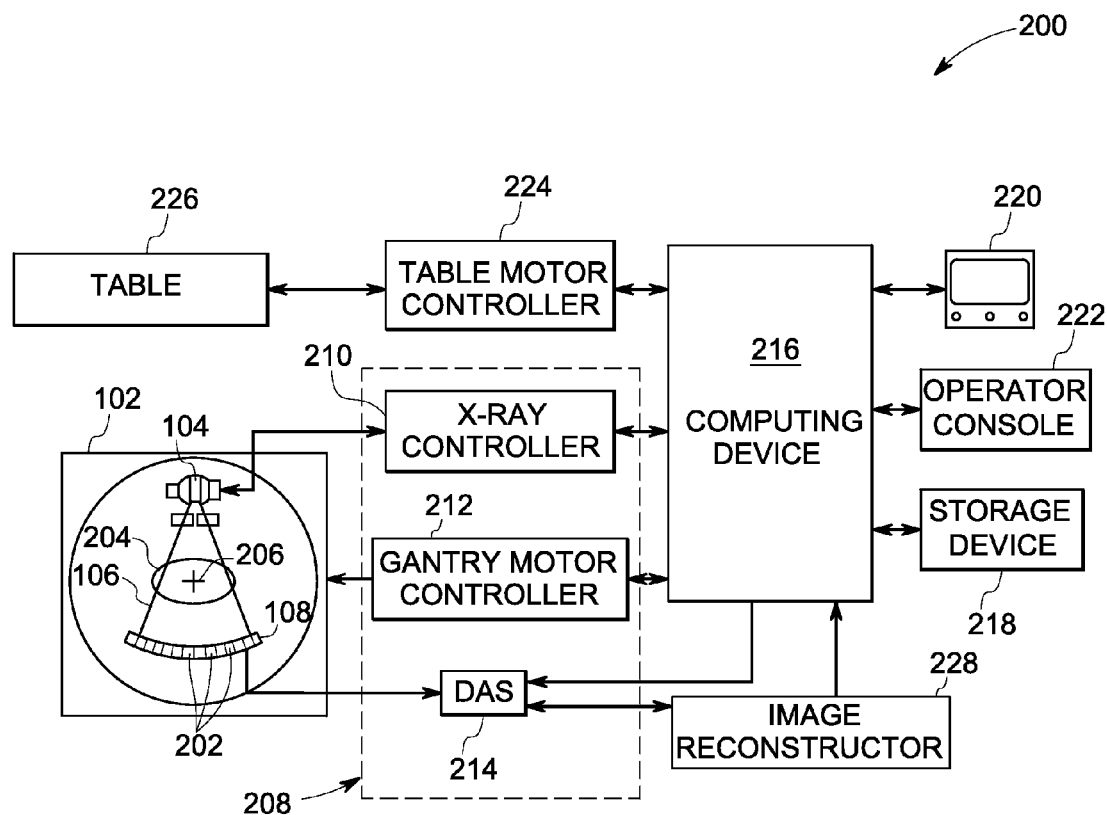
FIG. 2 is a block schematic diagram of an imaging system.

Further, FIG. 2 illustrates an imaging system 200, similar to the CT system 100 of FIG. 1, for acquiring and processing image data in accordance with aspects of the present technique. The imaging system 200, however, may differ from the CT system 100 in one or more structural and functional aspects. By way of example, the detector array 108 of the imaging system 200 may further include a plurality of detector elements 202 that together sense the projected X-ray beams that pass through an object 204, such as a medical patient or a baggage to acquire corresponding projection data.

Typically, during a scan to acquire projection data, the gantry 102 and the components mounted thereon rotate about a center of rotation 206. However, in certain embodiments where a projection angle relative to the object 204 varies as a function of time, the mounted components may move along a general curve rather than along a segment of a circle. Accordingly, the rotation of the gantry 102 and the operation of the X-ray radiation source 104 may be controlled by a control mechanism 208 of the imaging system 200 to acquire projection data from a desired view angle of the X-ray radiation source 104. In one embodiment, the control mechanism 208 may include an X-ray controller 210 that provides power and timing signals to the X-ray radiation source 104 and a gantry motor controller 212 that controls the rotational speed and position of the gantry 102. The control mechanism 208 may also include a data acquisition system (DAS) 214 for sampling analog data from the detector elements 202 and converting the analog data to digital signals for subsequent processing.

The data sampled and digitized by the DAS 214 is input to a computing device 216. The computing device 216 may store this data in a storage device 218, such as a floppy disk drive, a compact disk-read/write (CD-R/W) drive, or a Digital Versatile Disc (DVD) drive. Alternatively, an image reconstructor 228 may receive the sampled and digitized X-ray data from the DAS 214 and perform high-speed reconstruction. The computing device 216 may further process the reconstructed image and/or store the reconstructed image in the storage device 218.

Further, a display 220 may be communicatively coupled to the computing device 216 to allow an operator to observe object images and related data. In one embodiment, the computing device 216 may receive commands and scanning parameters from the operator via a console 222 that may include a keyboard (not shown). The computing device 216 uses the operator supplied and/or system defined commands and parameters to provide control signals and information to one or more of the DAS 214, the X-ray controller 210 and the gantry motor controller 212. Additionally, the computing device 216 may also operate a conveyor system controller or a table motor controller 224 that, in turn, controls a conveyor system or a motorized table 226. The table motor controller 224 may move the table 226 for appropriately positioning the object 204, such as the patient, in the gantry 102 to acquire corresponding image data.

The X-ray radiation source 104 used for imaging the object 204 is typically an X-ray tube that includes at least a cathode and an anode. Currently, X-ray tubes include an electron source to generate an electron beam that impinges on the anode to produce X-rays. The electron sources control the magnitude of the electron beam current by changing a current configuration of an X-ray filament, and therefore the emission temperature of the filament. These X-ray tubes, however, fail to effectively control electron beam intensity and focal spot size on a view-by-view basis based on scanning requirements, thus limiting imaging options. As used herein, the term "view" refers to a projection image acquired at a specific gantry angle or a frame in a projection X-ray image. Further, in accordance with aspects of the present technique, the X-ray radiation source 104 may correspond to an X-ray tube that provides microsecond current control and a wide range of focusable emission for improved X-ray images. An exemplary X-ray tube that enables microsecond current control for generating focal spots of a desired size and quality with optimal radiation dose is described in greater detail with reference to FIG. 3.

Figure 3:
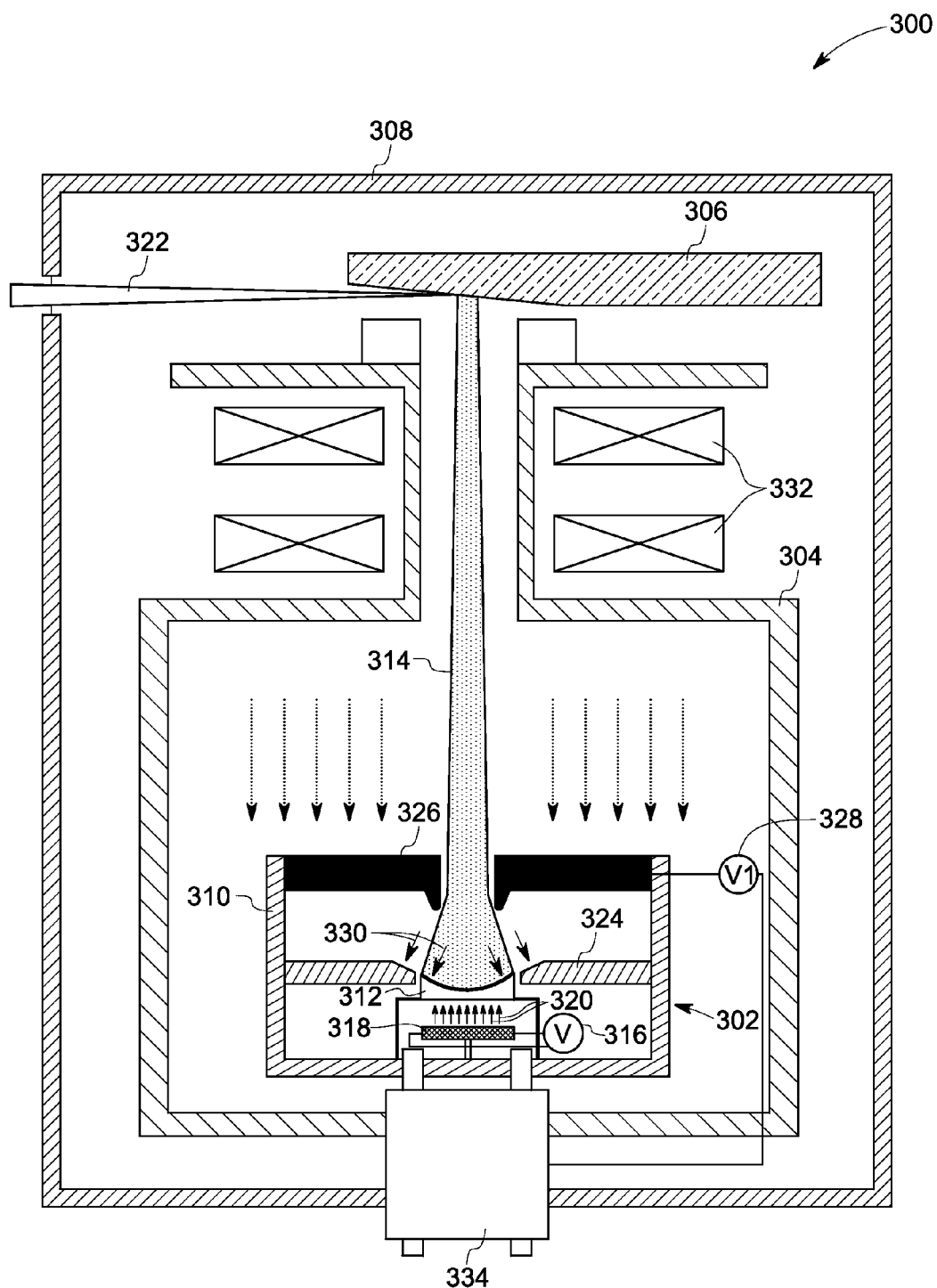
FIG. 3 is an illustration of an exemplary X-ray tube, in accordance with aspects of the present system.

FIG. 3 illustrates an exemplary X-ray tube 300, in accordance with aspects of the present technique. The X-ray tube 300 may be used as a radiation source in an imaging system such as the imaging system 200 illustrated in FIG. 2. In one embodiment, the X-ray tube 300 includes an injector 302 disposed within a vacuum wall 304. The X-ray tube 300 also includes an anode 306 that serves as a stationary or a rotating X-ray target (target 306). The target 306, along with the injector 302, is disposed within a tube casing 308. In accordance with aspects of the present technique, the injector 302 may further include one or more components enclosed within an injector wall 310. By way of example, the one or more components may include at least one cathode in the form of an emitter 312 for emitting an electron beam 314. Particularly, the emitter 312 may include a flat emission surface, a curved emission surface, or any other suitably shaped emission surface for emitting the electron beam 314 according to imaging requirements.

Further, in one embodiment, the emitter 312 is directly heated by passing a large current through the emitter 312 using a voltage source 316 coupled to the emitter 312. The large current heats the emitter 312, thus causing emission of the electron beam 314. Alternatively, the emitter 312 may be heated indirectly using a thermionic electron source 318 that generates electrons when subjected to appropriate heating conditions. To that end, the thermionic electron source 318 may comprise a material having a high melting point, stable electron emission at high temperatures, low work-function, or combinations thereof. Accordingly, the thermionic electron source 318 may be heated by passing a current and/or applying a voltage across the thermionic electron source 318 using, for example, a filament lead or the voltage source 316. The heated thermionic electron source 318 then generates electrons that may generally be referred to as a heating electron beam 320. The emitter 312 when impinged upon by the heating electron beam 320 generates the electron beam 314.

The electron beam 314 generated by the emitter 312 is focused towards the target 306 to generate X-rays 322 using a focusing electrode 324. The focusing electrode 324 is maintained at a suitable potential, for example at a negative potential with respect to the emitter 312, to focus the electron beam 314 away from the focusing electrode 324 and towards the target 306. Alternatively, the focusing electrode 324 may be maintained at a voltage potential that is equal to or substantially similar to a voltage potential of the emitter 312 for generating a parallel electron beam.

Further, the injector 302 may also include at least one extraction electrode 326 for controlling and/or focusing the electron beam 314 towards the target 306. To that end, the X-ray tube 300 may include a bias voltage power supply 328 that supplies a suitable voltage for maintaining the extraction electrode 326 at a positive bias voltage or a negative bias voltage with respect to the emitter 312. In certain embodiments, the extraction electrode 326 may further be divided into a plurality of regions having different voltage potentials to perform focusing and/or a biased emission of the electron beam 314 from different regions of the emitter 312.

In accordance with aspects of the present technique, the extraction electrode 326 and/or the focusing electrode 324 may be used for controlling the electron beam current in the X-ray tube 300. To that end, the extraction electrode 326 may be biased at a positive voltage with respect to the focusing electrode 324, thus creating a potential difference between the extraction electrode 326 and the focusing electrode 324. The potential difference between the extraction electrode 326 and the focusing electrode 324 generates an electric field 330 that may be employed to control the intensity of electron beam 314.

Particularly, the electric field 330 causes the electrons emitted from the emitter 312 to be accelerated towards the target 306. In one embodiment, the stronger the electric field 330, the greater is the acceleration of the electrons from the emitter 312 towards the target 306. Alternatively, the weaker the electric field 330, the lesser is the acceleration of electrons from the emitter 312 towards the target 306. Accordingly, the strength of the electric field 330 may be adjusted, for example, by varying the voltage potential (kV) of the extraction electrode 326 using a voltage tab (not shown) coupled to the bias voltage power supply 328 to control the electron beam intensity.

Further, in certain embodiments, a magnetic assembly 332 disposed between the injector 302 and the target 306 may provide additional control of the electron beam 314. Particularly, the magnetic assembly 332 may include one or more multipole magnets that influence the focusing of the electron beam 314 by creating a magnetic field that shapes the electron beam 314 on the X-ray target 306. By way of example, the one or more multipole magnets may include one or more quadrupole magnets, one or more dipole magnets, or combinations thereof. In one embodiment, the one or more multipole magnets generate the magnetic field for deflecting and/or positioning the electron beam 314 towards the target 306 as a function of an energy level of the electron beam 314. The magnetic field, thus generated, may further be controllable from a steady state to a sub-30 microsecond time scale for a wide range of focal spot sizes generated by the injector 302.

While employing the injector 302 in an imaging device such as a CT system, the electron beam current has to be quickly modified, typically in the order of 10s of microseconds to optimize the image quality and dose to a patient. As previously noted, rapid changes in the electron beam current and voltage, however, may cause rapid changes in the space charge effects and the electro-magnetic focusing in the injector 302, especially while operating within a determined range of current values. By way of example, the determined range may correspond to current values from about 10 mA to about 1500 mA at about 80 kV. While operating the injector 302 at a low electron beam current that falls within the determined range, such as about 10 mA, the electro-magnetic forces generated by the electric field 330 and the magnetic assembly 332 may influence the positioning of the electron beam 314 and the focal spot size and quality.

Accordingly, in one embodiment, pulse width modulation (PWM) is used to modulate the duty cycle of the electron beam 314 to avoid any disruptive influence of the electromagnetic forces on the positioning and the focusing of the electron beam 314 at low currents. As used herein, the term "duty cycle" refers to a ratio of the electron beam "on" time to a particular view time.

Typically, a detector in the CT system is operated in an integrated signal mode such that output of an X-ray signal is proportional to the X-ray integration over a particular view time. By way of example, each view time of the X-ray tube 300 may correspond to about 20 microseconds to about 500 microseconds. Further, a series of pulses may be generated by rapidly switching the electron beam intensity during the particular view time. The integrated X-ray signal within the particular view time, therefore, is proportional to a peak X-ray signal and a duty cycle of the series of pulses generated within the particular view time. In the presently contemplated configuration, the duty cycle of the series of pulses generated within a specific view of the X-ray tube 300 is adapted to generate at least a determined X-ray flux for a specific view of the X-ray tube 300. Particularly, in one embodiment, the injector 302 employs PWM to vary the duty cycle of the series of pulses generated within the specific view of the X-ray tube 300. An exemplary PWM scheme that may be employed by the injector 302 to modulate the duty cycle of the electron beam 314 is illustrated in FIG. 4.

Figure 4:
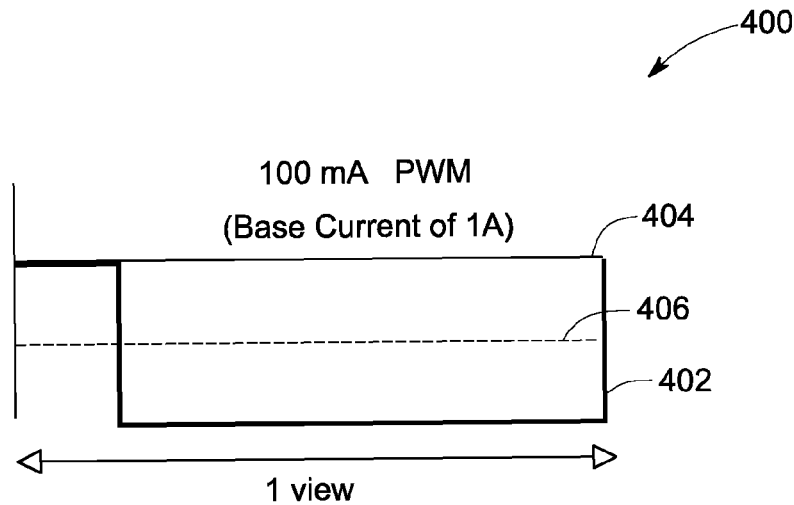
FIG. 4 is a graphical representation of an exemplary waveform for modulating a duty cycle of the electron beam, in accordance with aspects of the present technique.

FIG. 4 illustrates a graphical representation 400 of an exemplary PWM waveform 402 corresponding to a specific view of an imaging system such as the CT system 200 of FIG. 2 in accordance with aspects of the present technique. To that end, a pulse width of a rectangular PWM pulse wave is modulated to vary an average value of the PWM waveform 402. The PWM waveform 402 is then used to rapidly switch, for example, the power to the bias voltage power supply 328 on and off several times during the specific view of the X-ray tube 300. Variations in the bias voltage power supply 328 vary the voltage across the extraction electrode 326 and thus the electron beam intensity. The PWM waveform 402, thus, modulates the duty cycle of the series of pulses generated during the specific view time to either convey information to one or more components of the imaging system or control an amount of power delivered to the injector 302 for controlling electron beam intensity.

Particularly, an equivalent value of mA within the specific view of the imaging system may be varied by varying a percentage of on-time of the PWM waveform 402 for operating the injector 302 at a high mA value and a low mA value. A exemplary relationship between the equivalent value of mA within the specific view and the percentage of on-time of the PWM waveform 402 for high mA value and low mA value operation may be defined as:

$$\text{Equivalent mA} = \text{High\_mA} * P\_\text{high} + \text{Low\_mA} * P\_\text{low} \quad (1)$$

where High_mA is a high emitter current value, P_high is a percentage (in time) of the high mA value and Low_mA is a low emitter current value and P_low is a percentage of the low mA value. By way of example, in a first mode of operation, the injector 302 may modulate a PWM waveform 402 using a High_mA of 1A (emitter current) with a P_high of about 10% (10% duty cycle) and P_low 404 of about 90% to produce a substantially equivalent mA 406 of about 100 mA as produced in a second mode of operation.

In the second mode of operation, the injector 302 may modulate a waveform 404 to generate an electron beam using a High_mA of 100 mA with a P_high of about 100% and a P_low of about 0%. The generated electron beam, however, may lose focus due to the disruptive electro-magnetic forces prevalent during low mA operation of the injector 302. The injector 302, thus, employs duty cycle modulation for operating the X-ray tube 300 in the first mode that uses a high current for generating the focal spot size, focal spot location, focal spot quality, electron beam intensity and/or position corresponding to the second mode of operation. Further, supplying power to the injector 302 for only a portion of the specific view time for varying the duty cycle of the electron beam reduces radiation effects and prolongs life of the X-ray tube 300.

With returning reference to FIG. 3, in one embodiment, the X-ray tube 300 includes a beam control unit 334 for varying the duty cycle of the electron beam based on imaging requirements. To that end, the beam control unit 334 may include, for example, a field programmable gate array (FPGA), a microprocessor, an application specific integrated circuit (ASIC), or any other suitable control device. In certain embodiments, instead of the beam control unit 334, a controlling subsystem such as the control mechanism 208, the X-ray controller 210 or the computing device 216 coupled to an imaging system such as the imaging system 200 of FIG. 2 may perform one or more functions of the beam control unit 334. The beam control unit 334 that modulates the duty cycle of the electron beam 314 at determined current values to generate a determined focal spot size, a determined focal spot location and/or a determined flux in the X-ray tube 300 will be described in greater detail with reference to FIG. 5.

Figure 5:
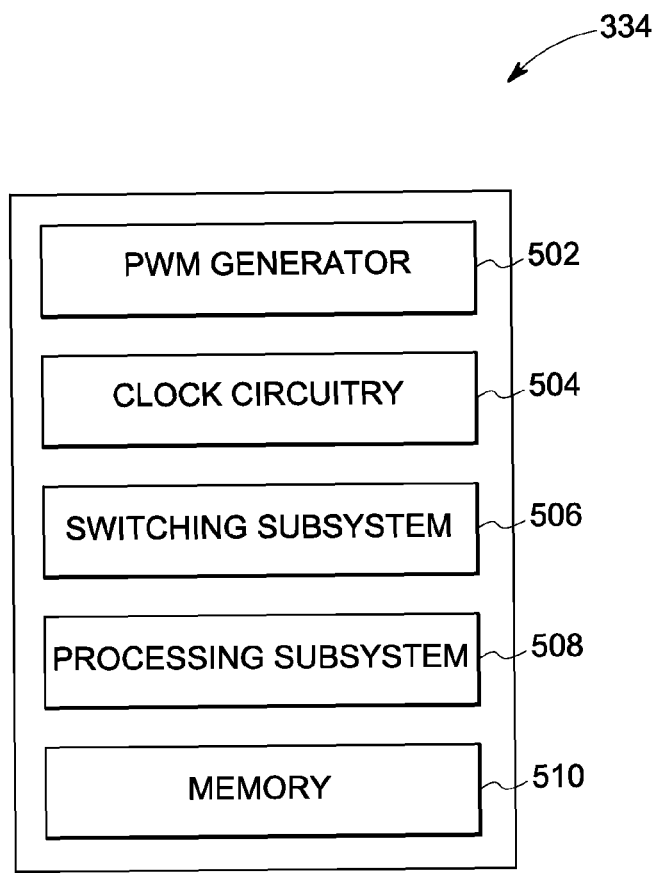
FIG. 5 is an illustration of exemplary components of the beam control unit illustrated in FIG. 3.

FIG. 5 illustrates a block diagram depicting exemplary components of the beam control unit 334 of FIG. 3. As previously noted, the beam control unit 334 modulates the duty cycle of the electron beam 314 at determined current values dynamically in near real time and/or according to a determined scanning procedure during imaging. Accordingly, in one embodiment, the beam control unit 334 includes a PWM generator 502, clock circuitry 504 and a switching subsystem 506 for varying the duty cycle of the series of pulses generated within a specific view time. In one embodiment, the beam control unit 334 provides digital control signals to the voltage source 316 of FIG. 3 for varying the voltage configuration corresponding to the extraction electrode 326 of FIG. 3 to control the intensity of the electron beam 314. Alternatively, the beam control unit 334 may apply a negative voltage to the extraction electrode 326 to prevent electron emission altogether.

In certain embodiments, the beam control unit 334 further includes a processing subsystem 508 and a memory 510 to determine suitable operational settings for the extraction electrode 326 and other imaging system components. Alternatively, in certain embodiments, the beam control unit 334 may be communicatively coupled to the processing subsystem 508 and the memory 510 over a wired and/or a wireless communications network, for example, the Internet for determining the operational settings. By way of example, when implementing the beam control unit 334 in an imaging system such as the imaging system 200 of FIG. 2, the processing subsystem 508 may correspond to the computing device 216 and the memory 510 may correspond to the storage device 218 of FIG. 2. Particularly, the beam control unit 334 uses the processing subsystem 508 to determine suitable operational settings for imaging the specific view of the X-ray tube 300 so as to generate at least a determined X-ray flux, a determined focal spot location and/or a determined focal spot size. By way of example, the operational settings may include a pulse width, a duty cycle, an electron beam switching frequency, an extraction voltage, a bias voltage, a magnet current and/or a gantry angle of an imaging system.

Further, in accordance with aspects of the present technique, the beam control unit 334 identifies a current configuration corresponding to a particular view of the X-ray tube 300 while performing a specific scanning procedure, such as a scout scan. As used herein, the term "current configuration" refers to a magnitude of the electron beam current (mA) between the emitter 312 and target 306 that serves as the anode in the X-ray tube 300 and/or the overall integration of this electron beam current over a specific imaging time. The beam control unit 334 identifies the current configuration used during the scanning procedure by employing, for example, a current probe or sensor (not shown) disposed close to the emitter 312. The current probe may determine the current configuration corresponding to the particular view of the X-ray tube 300 and transmit a signal indicative of the identified current configuration back to the beam control unit 334 via an electrical lead (not shown). In one embodiment, the beam control unit 334 further determines a determined focal spot size, a determined focal spot location and/or a determined X-ray flux for imaging an object. By way of example, while imaging a patient at 1250 mA and 80 kV, the determined focal spot size may correspond to 6.8 mm×2.1 mm In certain embodiments, a user may supply values corresponding to the determined X-ray flux, a determined focal spot location and/or the determined focal spot size via an input device (not shown) coupled to the beam control unit 334. In certain other embodiments, the processing subsystem 508 determines the determined X-ray flux, a determined focal spot location and/or the determined focal spot size based on the specific scanning procedure used for imaging. To that end, the memory 510 may store a correlation between specific scanning procedures and corresponding X-ray flux, focal spot characteristics and/or a current configuration corresponding to different views of the injector 302.

In one embodiment, if the identified current configuration is outside the determined range (PWM range), the beam control unit 302 employs a continuous focusing scheme. Particularly, the beam control unit 334 employs the continuous focusing scheme at current values higher than the PWM range, for example at current values greater than 400 mA, to directly regulate the electron beam current incident on the target 306 when imaging the particular view. In certain embodiments, the beam control unit 334 regulates the electron beam current by rapidly switching the electron beam 314 on and off in the order of microseconds to transmit signals that regulate image data acquisition during the particular view. In certain embodiments, the beam control unit 334 regulates the electron beam current, for example, by applying a negative voltage to the focusing electrode 324, varying a voltage configuration corresponding to the extraction electrode 326 to change the electron beam current and/or applying a negative voltage to the extraction electrode 326 to completely turn off the electron beam 314.

If the identified current configuration, however, is within the determined range, the beam control unit 334 uses the switching subsystem 506 for enabling the PWM mode. The beam control unit 334, in one embodiment, may further configure the extraction voltage to set the electron beam current at a determined value, such as about 400 mA. Additionally, the beam control unit 334 configures the bias voltage power supply 328 to apply an appropriate voltage across the extraction electrode 326 to enable the emitter 312 to generate an electron beam current having the determined value.

Further, the beam control unit 334 employs the processing subsystem 508 to determine the operational settings such as a pulse width, a switching frequency, and a duty cycle to be applied to the bias voltage power supply 328 to generate a PWM waveform that regulates the extraction voltage and thus the electron beam current. Particularly, the processing subsystem 508 determines the operational settings so as to generate the determined X-ray flux, a determined focal spot location and/or the determined focal spot size based on the determined value of the electron beam current. Additionally, the processing subsystem 508 may also determine operational settings for other system components such as the focusing electrode 324 and/or the magnetic assembly 332 based on the determined value of the electron beam current to ensure precise focusing of the electron beam 314.

Accordingly, in one embodiment, the PWM generator 502 employs the clock circuitry 504 and the switching subsystem 506 to generate a suitable PWM waveform to be applied to the voltage source 316 using the determined switching frequency. To that end, the switching subsystem 506 may include devices such as a transistor, a MOSFET switch, or any other suitable device coupled to the voltage source 316 and/or the bias voltage power supply 328 for applying appropriate voltage values across at least the extraction electrode 326 as a function of time.

Particularly, the PWM generator 502 uses the switching subsystem 506 and the clock circuitry 504 to generate a PWM waveform having the pulse width and the duty cycle determined by the processing subsystem 508. In certain embodiments, the PWM waveform varies the duty cycle by either varying the pulse width of the PWM waveform while maintaining a constant frequency or by varying the number of pulses provided while maintaining a constant pulse width. Alternatively, both the pulse width and the frequency may be varied to achieve the determined duty cycle. In certain other embodiments, the PWM waveform may also vary the duty cycle by varying one or more parameters corresponding to the duty cycle such as cycle time, frequency, intensity, phase and number of pulses. The beam control unit 334, thus, uses the generated PWM waveform to vary the voltage supplied to the extraction electrode 326 to modulate the duty cycle of the electron beam 314 for the specific view of the X-ray tube 300.

The modulated electron beam 314 is then focused and positioned by the electro-magnetic forces to impinge upon the target 306 to generate the X-rays 322. The X-rays 322, thus generated, produce the determined X-ray flux corresponding to, for example, a low current operation of the injector 302 even while operating in a high current mode. Duty cycle modulation, thus, enables the injector 302 to achieve a large equivalent range of X-ray flux within one view without requiring the injector 302 to have a wide dynamic current range. An exemplary method for modulating a duty cycle of an X-ray beam to enable an electron gun to operate in a wide modulated current while achieving high image quality and optimized dose control is described in greater detail with reference to FIGS. 6-7.

Figure 6:
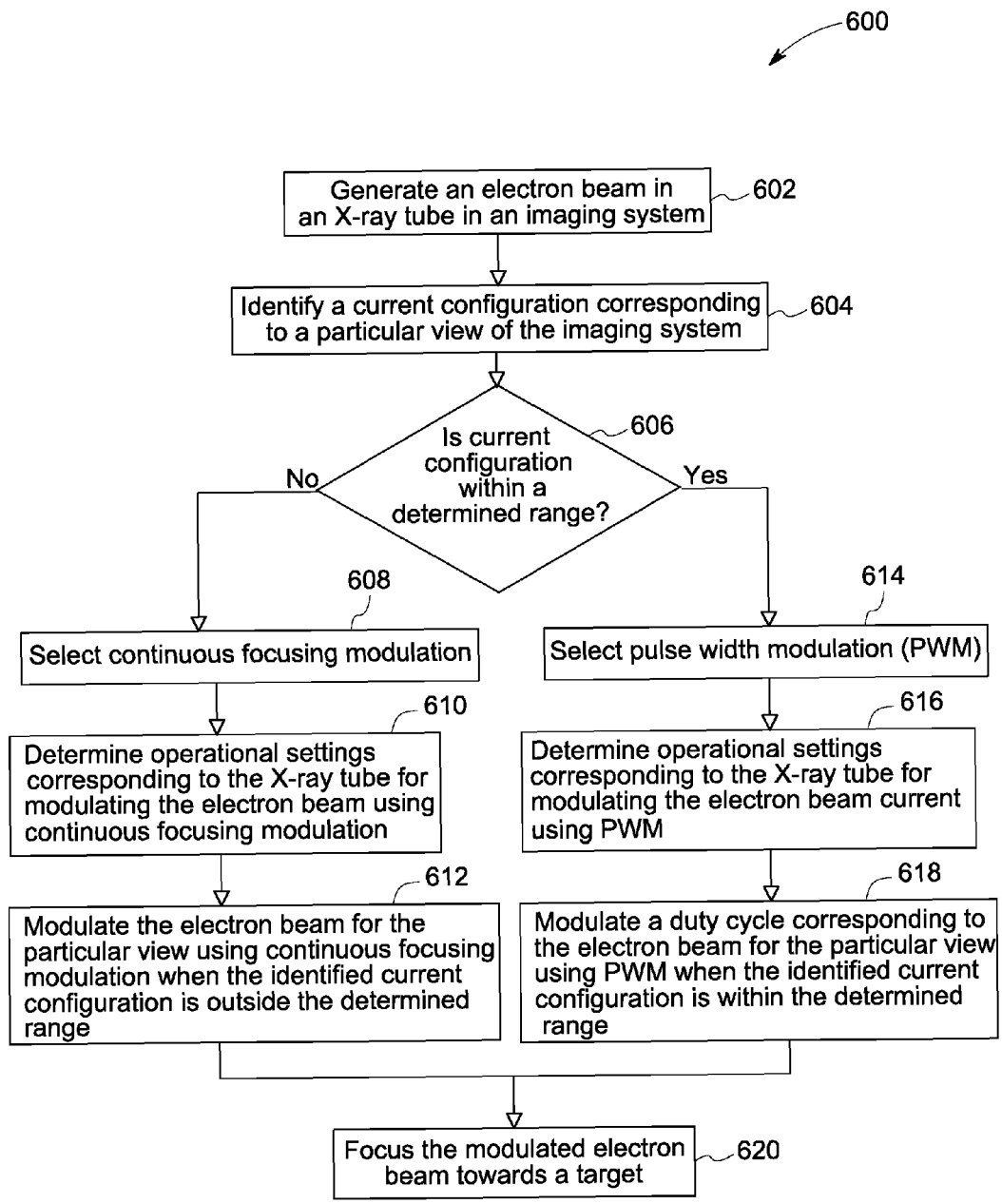
FIG. 6 is a flow chart depicting an exemplary method for operating an electron beam system, in accordance with aspects of the present technique.

Turning to FIG. 6, a flow chart 600 depicting an exemplary method for operating an electron beam system such as the injector 302 of FIG. 3 is presented. The exemplary method may be described in a general context of computer executable instructions on a computing system or a processor. Generally, computer executable instructions may include routines, programs, objects, components, data structures, procedures, modules, functions, and the like that perform particular functions or implement particular abstract data types. The exemplary method may also be practiced in a distributed computing environment where optimization functions are performed by remote processing devices that are linked through a communication network. In the distributed computing environment, the computer executable instructions may be located in both local and remote computer storage media, including memory storage devices.

Further, in FIG. 6, the exemplary method is illustrated as a collection of blocks in a logical flow chart, which represents a sequence of operations that may be implemented in hardware, software, or combinations thereof. The various operations are depicted in the blocks to illustrate the functions that are performed generally during electron beam generation, current configuration identification, modulation and focusing phases of the exemplary method. In the context of software, the blocks represent computer instructions that, when executed by one or more processing subsystems, perform the recited operations of an electron beam system. The order in which the exemplary method is described is not intended to be construed as a limitation, and any number of the described blocks may be combined in any order to implement the exemplary method disclosed herein, or an equivalent alternative method. Additionally, individual blocks may be deleted from the exemplary method without departing from the spirit and scope of the subject matter described herein. For discussion purposes, the exemplary method will be described with reference to the elements of FIGS. 1-5.

The exemplary method aims to enable the electron beam system, such as the injector 302 of FIG. 3, in an imaging system such as the imaging system 200 of FIG. 2 to operate in a wide dynamic focusable range. Accordingly, at step 602, an emitter such as the emitter 312 in the electron injector generates an electron beam. In one embodiment, as described with reference to the emitter 312 of FIG. 3, the emitter may directly or indirectly be heated to generate the electron beam. Subsequently, the heating electron beam impinges upon the emitter to generate the electron beam that may be used for imaging a person, a bag, or any other suitable object.

Further, at step 604, a current configuration corresponding to a particular view of the imaging system while performing a specific scanning procedure is identified. By way of example, the identified current configuration may correspond to a magnitude of the electron beam current generated by the emitter for scanning the particular view of the imaging system. In certain embodiments, a user may supply the current configuration using an input device coupled to the imaging system. Alternatively, the processing unit may infer the current configuration corresponding to the particular view of the imaging system based on the specific scanning procedure being performed and/or characteristics of the object being imaged.

The identified current configuration may then be compared against a determined range of values corresponding to the electron beam current at step 606. By way of example, the determined range may correspond to current values from 50 mA to 400 mA. In one embodiment, the determined range corresponds to a range of current values at which the electron beam may narrow considerably due to the effects of the electro-magnetic forces.

If the identified current configuration is outside the determined range, a control unit such as the beam control unit 334 enables the electron injector to operate in continuous focusing mode at step 608. Particularly, the control unit employs continuous focusing modulation for regulating the electron beam current incident on the target object. Accordingly, at step 610, the processing unit determines one or more operational settings corresponding to the electron injector and/or other components of the imaging system for modulating the electron beam current using continuous focusing modulation. By way of example, the processing unit may determine an extraction voltage for achieving a determined electron beam intensity, switching frequency for varying the voltage across the extraction electrode and/or a gantry angle for scanning a particular view of the imaging system based on the specific scanning procedure being used.

Further, at step 612, the control unit uses the determined operational settings for modulating the electron beam current using continuous focusing modulation. By way of example, the control unit uses a switching module such as the switching subsystem 506 for varying a voltage configuration corresponding to the extraction electrode 326 in intervals of about 1-15 microseconds to intervals of about at least 150 milliseconds. Variations in the voltage configuration corresponding to the extraction electrode 326 modulates the electron beam intensity in intervals of the order of microseconds, thus achieving microsecond intensity switching of the electron beam.

Referring back to step 606, if the identified current configuration is within the determined range, the control unit uses the switching module to select the PWM mode of operation for the electron injector at step 614. The PWM mode of operation of the electron injector will be described in greater detail in the following sections with reference to FIG. 6.

Further, at step 616, the processing unit determines one or more operational settings for operating the electron injector and/or one or more components of the imaging system in the PWM mode. By way of example, the processing unit may determine a pulse width, a duty cycle of a series of pulses generated with a particular view of the imaging system, switching frequency and/or extraction voltage. Particularly, the processing unit determines the operational settings so as to generate a determined X-ray flux, a determined focal spot location and/or a determined focal spot size based on requirements of the specific scanning procedure being used. As previously noted, the determined flux, a determined focal spot location and the determined focal spot size may be supplied by a user via an input device (not shown) coupled to the imaging system. Alternatively, the processing unit determines the determined X-ray flux, a determined focal spot location and/or the determined focal spot size based on the specific scanning procedure and a current configuration used for imaging.

Subsequently, at step 618, the control unit uses the determined operational settings to modulate the duty cycle of the electron beam for the particular view of the imaging system using PWM. Accordingly, in one embodiment, the control unit uses the switching module to rapidly switch the electron injector on and off to generate a series of pulses within the particular view time of the imaging system. By way of example, each view time of the imaging system may correspond to about 20 microseconds to about 500 microseconds. The number of pulses generated within a particular view time may vary based on a transmit time of the series of pulses.

As previously noted, output of an X-ray signal is proportional to a peak X-ray signal and a duty cycle of the series of pulses generated within the particular view time. The duty cycle of the series of pulses, therefore, may be adapted using PWM as described with reference to FIG. 4 to generate an equivalent X-ray signal. Particularly, the equivalent X-ray signal may be determined based on a maximum X-ray signal, a minimum X-ray signal and the duty cycle of the series of pulses generated within the particular view time. Accordingly, for operating the electron injector in a determined current configuration, the imaging system uses duty cycle modulation to generate an equivalent X-ray signal instead of changing the electron beam current itself. Particularly, modulating the duty cycle of the electron beam instead of the directly varying the electron beam current to generate a determined flux improves the imaging speed of the imaging system while requiring reduced switching power.

Subsequently, at step 620, the modulated electron beam is focused and positioned by the electro-magnetic forces to impinge upon a target to generate X-rays. The X-rays, thus generated, produce the determined X-ray flux corresponding to a low current operation of the electron injector even while operating in a high current mode. Duty cycle modulation of the electron, thus, enables the electron injector to achieve a large equivalent range of X-ray flux within one view without requiring the electron injector to have a wide dynamic current range. Particularly, the ability of the imaging system to operate in multiple modes in different current configurations greatly enhances the imaging options available to the imaging system. A method for operating the electron injector in multiple modes in accordance with aspects of the present technique will be described in greater detail with reference to FIG. 7.

Figure 7:
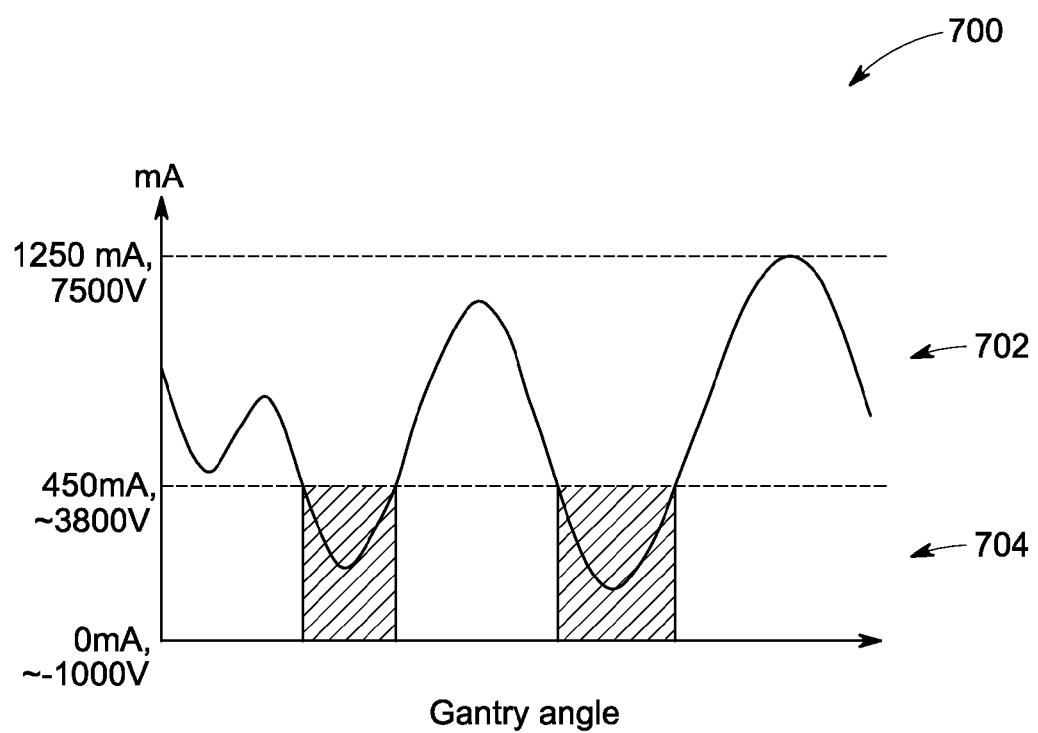
FIG. 7 is a graphical representation of exemplary modes of operation of an electron beam system in different current configurations, in accordance with aspects of the present technique.

FIG. 7 depicts a graphical representation 700 illustrating multiple modes of operation of an electron injector in different current configurations. Particularly, FIG. 7 depicts an exemplary operation of the electron injector in different modes based on a current configuration corresponding to a particular view of the imaging system. To that end, the imaging system identifies the current configuration corresponding to the particular view of the imaging system using the method described with reference to step 604 of FIG. 6. Subsequently, a control unit such as the beam control unit 334 of FIG. 3 selects the operation mode of the electron injector based on the identified current configuration.

In one embodiment, the control unit configures the electron injector to operate in the continuous focusing mode in a region 702 indicative of a high current configuration and the PWM mode in a region 704 indicative of a low current configuration. By way of example in the illustrated embodiment, the high current region 702 corresponds to current values between 450 mA and 1250 mA, with an extraction voltage of about 3500 V to 7500 V. Further, the low current region 704 corresponds to current values between 0 mA and 450 mA, with the extraction voltage between −1000 V and 3500 V. However, the low current region 704 and the high current region 702 may correspond to other values without departing from the spirit and scope of the invention. Moreover, in one embodiment, the low current region 704 may correspond to 200-450 mA and the beam may be used in continuous operation between 0-200 mA.

As described with reference to step 612, the electron injector employs continuous focusing modulation to regulate the electron beam intensity using microsecond intensity switching while operating in the high current region 702. Particularly, the control unit uses the switching module for varying a voltage configuration corresponding to the extraction electrode in intervals of about 1-15 microseconds to intervals of about at least 150 milliseconds. Variations in the voltage configuration corresponding to the extraction electrode modulates the electron beam intensity in intervals of the order of microseconds, thus improving data acquisition and imaging system performance.

Alternatively, the electron injector uses PWM to modulate the duty cycle of the electron beam for operating in the low current region 704. By way of example, the electron injector may operate in the low current region 704 while performing a scout scan where the electron injector uses a current configuration of about 10-50 mA and a stationary gantry. In one embodiment, the low current configuration corresponds to a user defined scanning procedure with the current configuration, for example, at about 200 mA at 80 kV for 5 seconds. In another embodiment, the low current configuration may correspond to a scanning mode that modulates the tube current as a function of a circumferential or an axial location to reduce dose administered to the patient without loss in image quality. Operating the electron injector using continuous focusing modulation in the low current region 704, however, may cause considerable narrowing of the electron beam causing loss of focus, and thus, image quality.

Accordingly, in one embodiment, the electron beam current may be set at a determined value, such as at about 1 A, at which the electron beam may avoid an overly narrowing effect of the electro-magnetic forces. Further, the processing unit may determine suitable operational settings for the particular view of the imaging system so as to generate the determined flux, a determined focal spot location and/or the determined focal spot size based on the determined value of the current. As previously noted, the operational settings may include a pulse width, a duty cycle, an electron beam switching frequency, an extraction voltage, a magnet current, a bias voltage and/or a gantry angle of the imaging system.

The control unit uses the determined operational settings to generate a suitable PWM waveform for varying a duty cycle of the series of pulses generated within the particular view of the imaging system. Particularly, the control unit uses the PWM waveform to provide digital control signals to the voltage source for varying the voltage configuration corresponding to the extraction electrode, thus controlling the duty cycle of the electron beam. Alternatively, the control unit may apply a determined negative voltage to the extraction electrode to prevent electron emission altogether. As described with reference to FIG. 4, the control unit may configure the extraction voltage to enable the electron injector operating in the low current region 704 to use 1A of emitter current with 10 percent duty cycle to produce an X-ray flux equivalent to a flux produced when operating with 100 mA and 100% duty cycle.

The electron injector, thus, employs duty cycle modulation for operating the electron injector at a high current while maintaining the focal spot size, focal spot quality, electron beam intensity and/or position for the particular view of the imaging system. Additionally, adapting the duty cycle of the electron beam while switching the electron injector from a high voltage configuration to a low voltage configuration during imaging preserves the signal-to-noise ratio of the electron beam. Further, the determined value of the electron beam current may be used subsequently during image reconstruction to account for variations in the voltage configuration of the electron injector to generate robust and high quality images using the modulated electron beam.

The systems and methods disclosed hereinabove, thus, greatly expand the current modulation range for an electron beam system by combining rapid control of electron beam current, X-ray flux and focal spot size generation using PWM. Additionally, duty cycle modulation of the electron beam enables the electron beam system to operate in multiple modes with microsecond intensity switching and a wide modulated mA and energy to achieve high quality imaging with optimized dose control.

Although the exemplary embodiments of the present system are described with reference to an electron injector in a CT system, use of the claimed electron beam system in any other suitable type of imaging device, such as an X-Ray system and an electron gun assembly using a Wehlnet cylinder or field electron emitters is also contemplated.

While only certain features of the present invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method comprising:
    generating an electron beam in an X-ray tube in an imaging system;
    identifying a current configuration corresponding to a particular view of the imaging system;
    modulating a duty cycle of the electron beam for the particular view of the imaging system using pulse width modulation when the identified current configuration is within a determined range; and
    focusing the modulated electron beam towards a target.

2. The method of claim 1, wherein modulating the duty cycle of the electron beam for the particular view of the imaging system comprises adapting the duty cycle so as to generate at least a determined X-ray flux.

3. The method of claim 2, further comprising determining operational settings corresponding to the X-ray tube for generating the determined X-ray flux, a determined focal spot size, a determined focal spot location, or combinations thereof, wherein the operational settings comprise a pulse width, a duty cycle, a frequency, a magnet current, a bias voltage, an extraction voltage, or combinations thereof.

4. The method of claim 2, wherein modulating the duty cycle of the electron beam for the particular view of the imaging system comprises adapting a duty cycle of a plurality of pulses generated within the particular view of the imaging system.

5. The method of claim 2, wherein modulating the duty cycle of the electron beam for the particular view of the imaging system comprises applying a negative voltage to an electrode in the X-ray tube to prevent electron emission, varying a voltage configuration corresponding to the electrode to change electron emission, or a combination thereof.

6. The method of claim 2, wherein modulating the duty cycle of the electron beam for the particular view of the imaging system comprises setting a current corresponding to the electron beam at a determined value.

7. The method of claim 6, further comprising using the determined value to account for variations in a voltage configuration corresponding to the X-ray tube during image reconstruction.

8. An electron beam system for an X-ray tube, comprising:
an emitter that generates an electron beam;
at least one electrode maintained at a positive bias voltage or a negative bias voltage with respect to the emitter, wherein the at least one electrode controls an intensity of the electron beam; and
a control unit coupled to the at least one electrode, wherein the control unit:
identifies a current configuration corresponding to the particular view of the X-ray tube; and
modulates a duty cycle of the electron beam for the particular view of the X-ray tube using pulse width modulation when the identified current configuration is within a determined range.

9. The electron beam system of claim 8, wherein the control unit varies the duty cycle of the electron beam for the particular view of the X-ray tube so as to generate at least a determined X-ray flux.

10. The electron beam system of claim 8, wherein the control unit varies the duty cycle of a plurality of pulses generated by the emitter within the particular view of the X-ray tube.

11. The electron beam system of claim 8, wherein the control unit modulates a duty cycle of the electron beam for the particular view of the X-ray tube by applying a negative voltage to the electrode to prevent electron emission, varying a voltage configuration corresponding to the electrode to change electron emission, or a combination thereof.

12. The electron beam system of claim 8, wherein the emitter is configured to generate an electron beam having a determined current value.

13. The electron beam system of claim 8, wherein the control unit selects continuous focusing modulation for modulating an electron beam current corresponding to the particular view of the X-ray tube when the identified current configuration is outside the determined range.

14. The electron beam system of claim 8, further comprising at least one focusing electrode disposed in proximity of the emitter, wherein the at least one focusing electrode focuses the electron beam, and wherein the at least one electrode is an extraction electrode.

15. An X-ray tube, comprising:
an electron beam system, comprising:
an emitter that generates an electron beam;
at least one electrode that controls an intensity of the electron beam, wherein the at least one electrode is maintained at a positive bias voltage or a negative bias voltage with respect to the emitter;
a control unit coupled to the at least one electrode, wherein the control unit:
identifies a current configuration corresponding to the particular view of the X-ray tube; and
modulates a duty cycle of the electron beam for the particular view of the X-ray tube using pulse width modulation when the identified current configuration is within a determined range; and
a target that generates X-rays when impinged upon by the electron beam.

16. The X-ray tube of claim 15, further comprising a magnetic assembly disposed between the electron beam system and the target and that directionally influences the electron beam towards the target.

17. The X-ray tube of claim 15, wherein the control unit varies the duty cycle of the electron beam for the particular view of the X-ray tube for generating at least a determined X-ray flux.

18. The X-ray tube of claim 15, wherein the control unit determines operational settings corresponding to the X-ray tube for generating the determined X-ray flux, a determined focal spot size, a determined focal spot location, or combinations thereof, wherein the operational settings comprise a pulse width, a duty cycle, a frequency, a magnet current, a bias voltage, an extraction voltage, or combinations thereof.

19. The X-ray tube of claim 15, wherein the control unit varies the duty cycle of a plurality of pulses generated by the emitter within the particular view of the X-ray tube.

20. The X-ray tube of claim 15, wherein the control unit modulates the duty cycle of the electron beam for the particular view of the X-ray tube by applying a negative voltage to the electrode, varying a voltage configuration corresponding to the electrode to change electron emission, or a combination thereof.

21. The X-ray tube of claim 15, wherein the emitter is configured to generate an electron beam having a determined current value.

22. The X-ray tube of claim 15, wherein the control unit selects continuous focusing modulation for modulating an electron beam current corresponding to the particular view of the X-ray tube when the identified current configuration is outside the determined range.

23. A computed tomography system, comprising;
a gantry;
an X-ray tube, comprising:
an electron beam system, comprising:
an emitter that generates an electron beam;
at least one electrode that controls an intensity of the electron beam, wherein the at least one electrode is maintained at a positive bias voltage or a negative bias voltage with respect to the emitter;
a control unit coupled to the at least one electrode, wherein the control unit:
identifies a current configuration corresponding to the particular view of the computed tomography system; and
modulates a duty cycle of the electron beam for the particular view of the computed tomography system using pulse width modulation when the identified current configuration is within a determined range;
a target that generates X-rays when impinged upon by the electron beam; and
one or more detector elements for detecting the attenuated electron beam from an object.

24. The computed tomography system of claim 23, further comprising a magnetic assembly disposed between the electron beam system and the target and that directionally influences the electron beam towards the target.

25. The computed tomography system of claim 23, wherein the emitter is configured to generate an electron beam having a determined current value.

26. The computed tomography system of claim 25, further comprising an image reconstruction unit that uses the determined current value to account for variations in a voltage configuration corresponding to the X-ray tube during image reconstruction.

27. The computed tomography system of claim 23, wherein the control unit selects continuous focusing modulation for modulating the electron beam corresponding to the particular view of the computed tomography system when the identified current configuration is outside the determined range.

* * * * *